United States Patent [19]

Lewis et al.

[11] 4,085,744
[45] Apr. 25, 1978

[54] SPINAL COLUMN PROSTHESES ORTHOSES

[76] Inventors: David Warren Lewis, Rte. 2, Box 198, Charlottesville, Va.; Robert K. Greenlaw, 708 George St., Sydney, Canada

[21] Appl. No.: 764,049

[22] Filed: Jan. 31, 1977

[51] Int. Cl.² ............................................. A61F 5/00
[52] U.S. Cl. ...................................... 128/69; 128/75; 128/78
[58] Field of Search .................. 128/69, 75, 78, 92 E, 128/92 B; 3/1.9

[56] References Cited
U.S. PATENT DOCUMENTS 3,565,066  2/1971  Roaf .................................. 128/78 X Primary Examiner—Robert W. Michell
Assistant Examiner—Michael H. Thaler

[57] ABSTRACT

These spinal column prostheses/orthoses are for the correction of problems involving scoliosis, kyphosis, spinal instability from a variety of causes, rotational and other mal-alignments by compression and/or distraction (tension) or a combination of these forces which are exerted at the inter spaces between two adjacent vertebrae. The force carried by each segment of these multi-segmented spinal column prostheses/orthoses may be adjusted at the time of insertion and re-adjusted at appropriate intervals as required. This implanted hardware may be used for children and/or adults, it will be constructed from the acceptable and medically approved implantable high quality metals, and may be left in place permanently or temporarily as may be required. Once the spinal correction has been made, the inserted hardware or a portion of it may be removed. These spinal column prostheses/orthoses afford the opportunity to apply forces initially small and later increased in magnitude; they provide the means for applying a given force and, as the device is accommodated and the spine shape corrected, to be readjusted, by certain elements external or internal to the body and thereby reestablish the prescribed force level. As implied by the title "Spinal Column Prostheses/Orthoses" this invention may be viewed as a prosthesis for one physiologic condition; may be used as an orthosis for another condition; and may be employed as a combination prosthesis/orthosis for another condition by the removal of a portion of the device upon partial physiologic correction.

2 Claims, 14 Drawing Figures

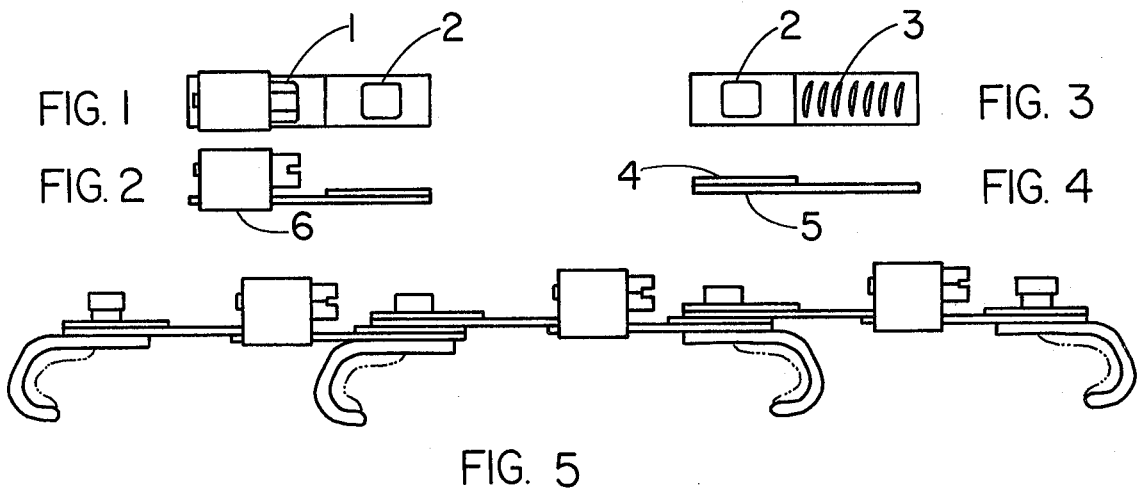
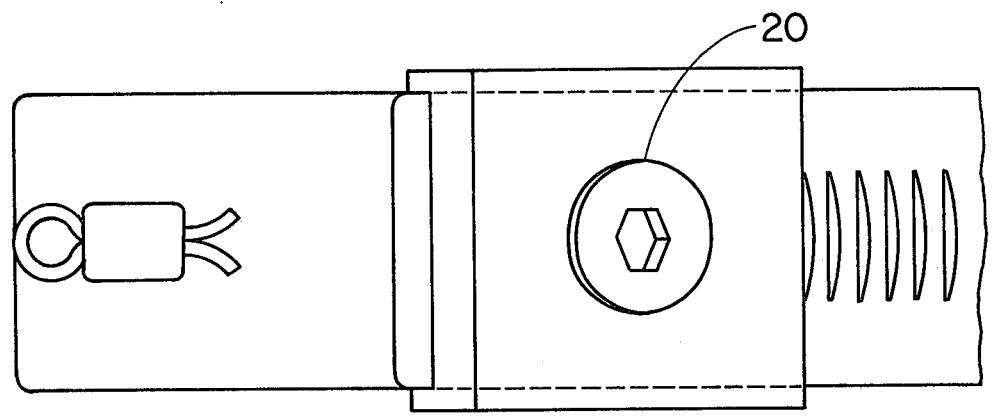
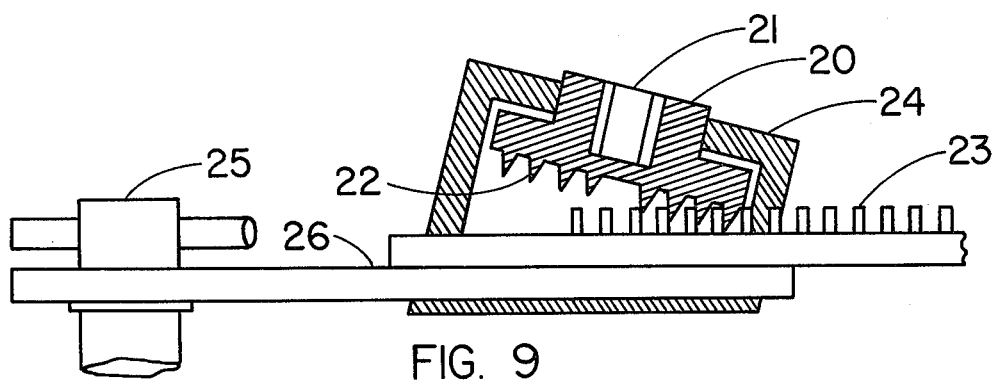

SPINAL COLUMN PROSTHESES ORTHOSES

BRIEF SUMMARY OF THE INVENTION

The spinal column prostheses/orthoses of the invention include hook elements, extension elements, and adjusting elements which taken in concert permit variations of extractive and compressive forces to be applied to pairs of vertebral bodies of the spine. The prescription of combinations of the named elements is made according to the need as determined by the physician. This is to imply that the use of the invention is not limited to one particular ailment or disease. Also, the description using the phrase "Prostheses/ortheses" is to note that for some application this invention will serve as a prosthesis implying a permanence in application yet the orthosis facet signifies the temporary nature in application of the invention.

This "spinal column prostheses/orthoses" carries with it the facility for adjustment without further major surgical intervention so that optimum use may be obtained by changing the overall dimensions of the invention during an extended period of time. This permits, also, the regulation or variation in the force distribution amongst the various vertebral bodies over a period of time measured in weeks so that the invention may be viewed as a "treatment" for improving the function of the musculature associated with the spine as well as a prosthetic/orthotic device.

The series of elements, which are interconnected, provide a certain flexibility when used for the compressive mode, making for ease of installation. Parts of the complete spinal column prosthesis/orthosis may be fitted in place before the remaining elements are brought to the surgical site. This simplifies the placement of the invention and is especially useful for the spinal problems involving curvature in more than a single plane where the installation of a rigid bar or rod would be unwieldy.

In general, the spinal column prosthesis/orthosis of this invention involves several elements which articulate together to form the whole. For application in the distraction (tension) mode, the elements, when loaded by appropriate forces, lock together into a rigid column.

Some of the general applications of this invention may be noted as follows:

To correct curvatures of the spine by compressing the convex side.

To correct curvatures of the spine by distracting (tension) the concave side.

The invention is of modular design so that as many vertebrae may be loaded with forces as required.

The invention shall also be capable of correcting or improving rotational malalignments.

These prostheses/orthoses will also be very useful for the correction of kyphosis, deformities, or instability of the spine as a result of spinal fractures, where the posterial elements are deficient, by either attaching the device to the transverse processes or the lateral processes or to the posterior aspect of the vertebral bodies.

This invention provides for periodic readjustment of forces without repeated major surgical intervention. The means for readjusting the invention external to the human body affords the physician the opportunity to "treat" the patient without the dangers associated with major surgical procedures; it also permits the treatment over extended periods of time and therefore minimizes the nonphysiological stress of a singularly applied correction whether through the standard rigid rods or high force level cables.

This invention may be used for children and adults who are encumbered with certain problems and diseases.

BRIEF DESCRIPTION OF THE DRAWINGS

The present invention will be better understood by reference to the attached drawings which show a preferred embodiment as well as alternate forms of these spinal column prostheses/orthoses.

FIG. 1 illustrates a preferred embodiment of this invention showing the tightening element by which the forces may be controlled.

FIG. 2 shows this same element except in a side view.

FIG. 3 illustrates a preferred embodiment of this invention and particularly the extention element as a top view.

FIG. 4 is a side view of the extension element shown in FIG. 3.

FIG. 5 illustrates the preferred embodiment of this invention showing how the various elements are arranged and interconnected when the spinal column prostheses/orthoses device is being used in the compressive mode.

FIG. 8 illustrates another possible or alternate embodiment of this invention showing it as a top view.

FIG. 9 is a partial section view of that alternate embodiment of FIG. 8.

DETAILED DESCRIPTION OF THE INVENTION

Figure 6:
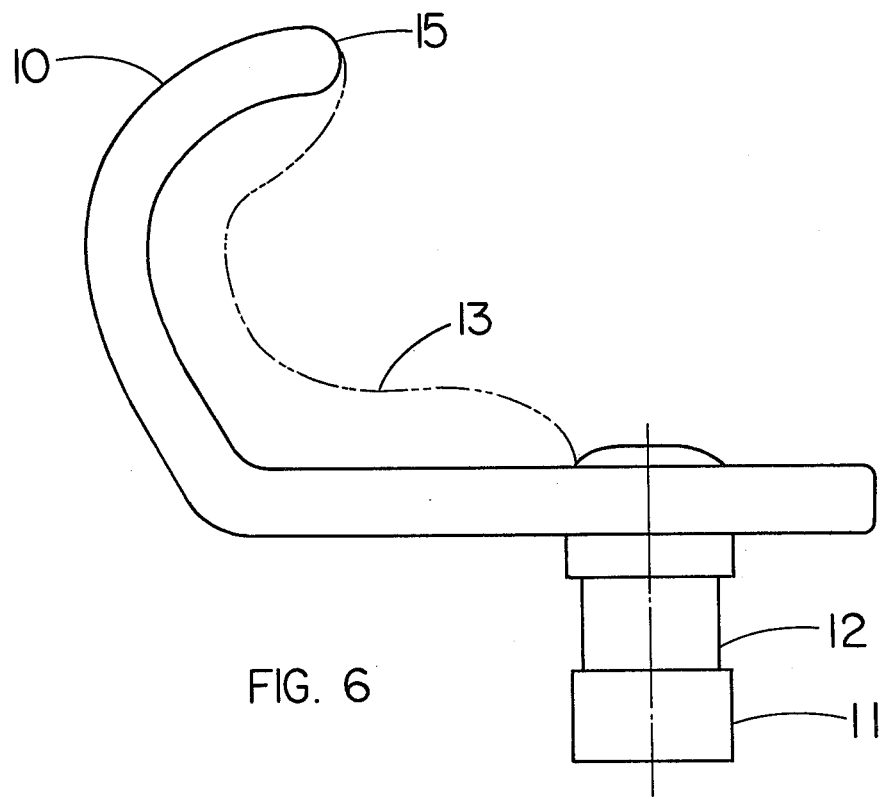
FIG. 6 is a side view detail of the load transfer element or hook element of this invention as a preferred embodiment.

This invention may be described as a unique combination of implantable elements and may be generally classified as a prosthesis/orthosis, the purpose of which is to correct problems involving scoliosis, kyphosis, spinal instability from a variety of causes, rotational, and other mal-alignments by compression or by distraction (tension) or combinations of these forces which are exerted through the interspace between two or more adjacent pairs of vertebrae. The force carried by each segment of these multi-segmented prostheses/orthoses may be adjusted for each space by the use of a special force gauge and adjusted at the time of insertion or implantation and readjusted at appropriate intervals as required. By suitable tools these readjustments may be made external to the patient without major surgical intervention. This implanted hardware may be used for children as well as adults; it will be constructed from acceptable and medically approved implantable materials and may be left in place permanently or temporarily according to the medical diagnosis. Once the spinal correction has been made, the inserted hardware or a portion of it may be removed or left implanted according to the judgement of the physician.

Some of the general features of this invention may be noted as follows: to correct curvatures by compressing the convex side of the spine and by distracting the concave side. The device is of modular design so that as many vertebrae as is necessary may be made captive and hence carry appropriate loads or forces. The device shall also be capable of correcting or improving rotational mal-alignments.

Force will be exerted on each transverse process or each vertebral body or lamina through the interspace of two vertebrae. Appropriate forces may be applied and concentrated where they are most needed. For example, more force may be applied at the apex of the spinal curvature than at the extremities of the curvature.

The forces may be adjusted for each interspace and readjusted as required as the curvature is reduced. This readjustment process may be made without major additional surgical intervention through use of unique adjusting tools compatible with this invention.

The device for correcting curvature or abnormalities of spinal alignment may be attached posteriorly, anteriorly, or laterally on the spinal element and at any level of the spinal column.

The small size of this prosthesis/orthosis will be such that adjustment can be made at any space as required.

This invention will also be very useful for the correction of kyphosis, deformity, or instability of the spine as a result of spinal fractures where the posterior elements are deficient, by either attaching the load transfer element or hook to the transverse processes or the lateral processes or to the posterior aspect of the vertebral bodies. The preferred embodiment of this design may be understood by studying the various figures. FIG. 1 shows one of the three main elements which in combination becomes the spinal column prosthesis/orthosis. FIG. 1 illustrates an adjusting device 1, which may be in the form of a helix such as the common screw thread, and a specially designed opening 2, the helix serving to allow this complete unit to engage a series of raised elements noted by 3 of FIG. 3. Clearance space is required for the insertion of element 3 into engagement with the helix portion 1. Alternatively, in place of raised elements 3, grooves or notches may be formed whereby the raised periphery of the helix will engage or osculate into these grooves. Either embodiment will serve this invention but whichever form is used, that particular form will have to be carried consistently to the adjacent and engaging elements.

The combination of attachment through the raised elements 3 of FIG. 3 or by grooved elements allow a force to be applied at one end of this adjusting element described by FIG. 1. Force may be transmitted to the other end through an appropriately self-locking pin 12 of FIG. 6 that will engage the hole 2 of FIG. 1. FIG. 5 shows a combination of three adjusting elements like those described by FIGS. 1 and 2, hooks like those described by FIGS. 6 and 7, and extension units as described by FIGS. 3 and 4. This combination of elements will allow force distribution over, for example, four adjacent transverse processes of the spine with adjustments to allow an optimal prescription of the distribution of these forces over the transverse processes or lamina. The individual adjustments permit different forces to be applied to successive vertebrae and progressively adjusted over several weeks of time as needed.

In FIG. 2 a shell 6 performs the function of holding the adjusting device in close proximity to the extension element such as described by FIG. 3. To provide more bearing surface the holes noted as 2 in FIG. 1 and FIG. 3 can be strengthened by use of double or multiple thicknesses of plates 4 and 5 of FIG. 4. The load transfer element or hook configuration that will attach to the, for example, transverse process is illustrated in FIG. 6. The special elements of this hook include an unusually shaped head 11 that will allow connection through the special hole shown by 2 in FIG. 3 and yet will be a retaining joint so that the combination of elements such as those of FIG. 1, FIG. 3, and FIG. 6 will be constrained as a chain allowing one to pick up a combination or array of elements, such as described in FIG. 5, without these elements becoming disengaged. The self-locking feature is due to the combination of appropriate shape and clearance or fit between the head 11 of FIG. 6 and a thin surface of the Silastic material (or equivalent) applied to that head and shank, 11 and 12, respectively, to act as a restraint. The bearing surface is through the shank 12 of FIG. 6 which is permanently affixed through welding or reveting to the main hook 10. The shape of this hook is rather sharp at the one extremity 15 of FIG. 6, and yet of such a shape having sufficient surface area and flatness from the main body of the hook 14 of FIG. 7 on down to the curved surface to the bearing surface 12 of FIG. 6 to distribute the extractive or compressive forces over a sufficient area of the processes of the spine so as to not disrupt them. To further insure good capatibility for oscullation between the hook and the appropriate spinal process a surface of Silastic or equivalent material is added to the innersurface of the hook shown as 13 of FIG. 6 and extending over the major portion of the interior section of the hook up to the sharp edge 15.

Figure 7:
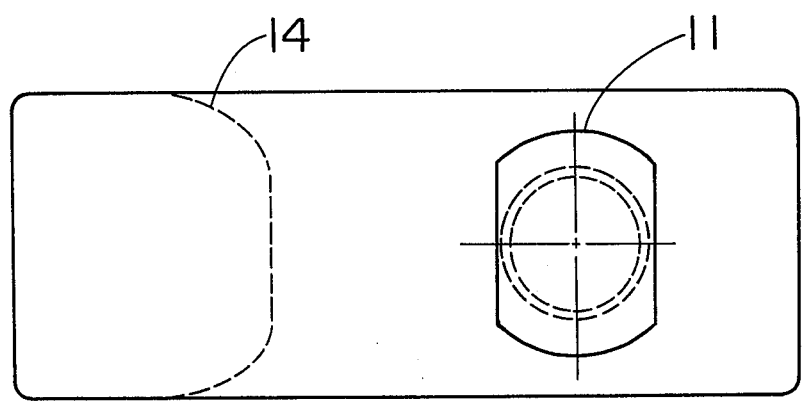
FIG. 7 shows a top view of the hook element presented in FIG. 6.

The engagement of the hook into the extension element noted by FIG. 3 may be accomplished by a 90° rotation of the hook relative to the opening or hole 2, and once the hook has been pushed through the hole, the Silastic cover over the cap 11 of FIG. 7 will act as a partial constraint to the elements being joined. However by 90° rotation of the hook relative to the extension element of FIG. 3, it will be impossible to remove the hook from this extension element due to the oversizeness of the head 11 of FIG. 7 relative to the hole opening 2 of FIGS. 1 or 3 depending upon whether the hook has been applied to the adjusting element, to the extension element, or to both as illustrated in FIG. 5.

The overall cross-section of the extension element illustrated by FIG. 3 will be a function of whether this unit is used for extraction forces on the spinal processes or whether it is to be used for applying compressive forces to the spinal processes. In the latter case the elements of FIGS. 1 and 3 will be primarily suffering tensile forces with no possibility of buckling, hence there will be less need for excessive amounts of materials for this application. However, the same configuration with but greater thickness of the material of FIGS. 1 and 3 will permit use of this device in an extractive mode. In this latter application the elements will be suffering compressive forces and hence must be capable of withstanding sufficient forces to prevent buckling of the overall unit. The configuration shown in FIG. 5 is for application for supplying compressive forces to the spine over adjacent spinal processes. By simply rotating the directions of the hooks, that is by 180° rotation about the bearing axis of each hook of FIG. 5 (this axis is shown as a centerline in FIG. 6), the figure would then represent this invention in the mode for extractive forces being applied to the spinous processes.

It is to be noted in passing that the various elements previously described will be of such dimensions so that those to be used in the compressive mode will not engage with those to be used in the extraactive mode. This will be for the sole purpose of safety so that the so called "column action mode of failure" will be avoided for the application of this invention for producing extractive forces. Another safety feature will be automatically built in through the fact that the elements used as extractive spinal column prostheses/orthoses will be thicker so that the bearing surface 12 of FIG. 6 will of necessity be longer in length.

FIG. 8 shows another possible configuration alternative of this invention in which instead of an adjusting screw, as depicted in FIG. 1, loading would be accomplished by a planar helical groove cut in a flat disk. This is noted by 20 in which a means of applying a torque to this planar helix would be through a hexagonal drive into the recess 21 of FIG. 9.

FIG. 9 is a side view of the invention depicted in FIG. 8 in which with raised portions 23 may be engaged by the plannar helix, with the teeth noted as 22, which is held by a housing 24 and an extending element 26. This extension may be affixed to similar units that would behave like the series of units depicted in FIG. 5.

Figure 10:
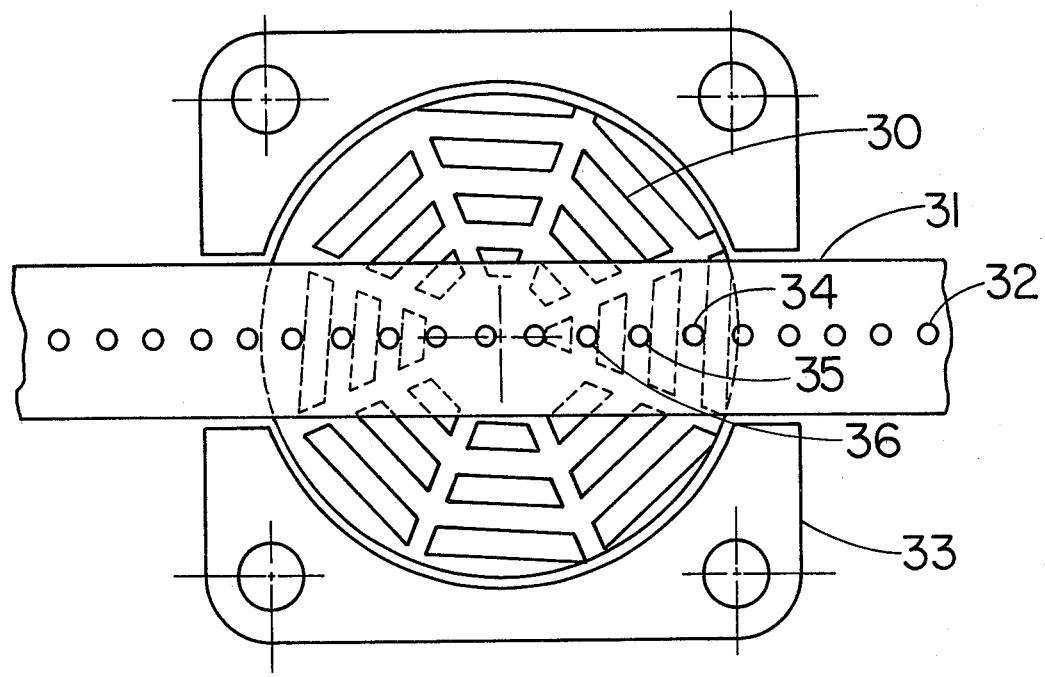
FIG. 10 is yet another alternate embodiment of this invention showing essentially a top view which has been partially sectioned to reveal some details in the interior.
Figure 11:
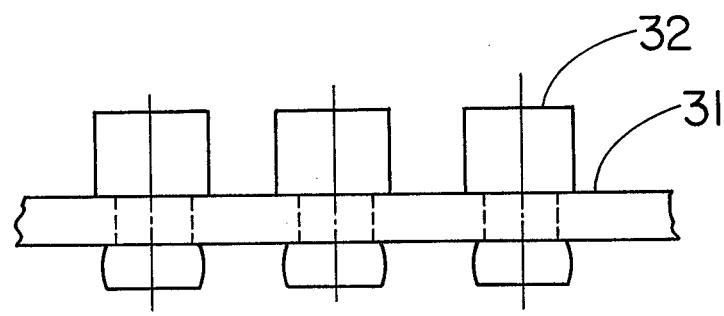
FIG. 11 is a side view of the extension element that would be associated with the particular configuration noted in FIG. 10.

Another embodiment of this invention is noted in FIG. 10 in which the helix of FIG. 9 has been replaced by a series of straight segments 30 which engage a series of pins 32 which are attached to the load carrying tape 31. FIG. 10 shows the meshing of three pins 34, 35, and 36 with the drive unit 30, the details of which have been omitted to show the geometric intermeshing. The main housing for this is noted as 33 of FIG. 10. An enlarged view of the tape is shown in FIG. 11, the tape being identified as 31 with the pegs or pins 32 through which the load would be transferred by the tightening head of FIG. 10.

Figure 12:
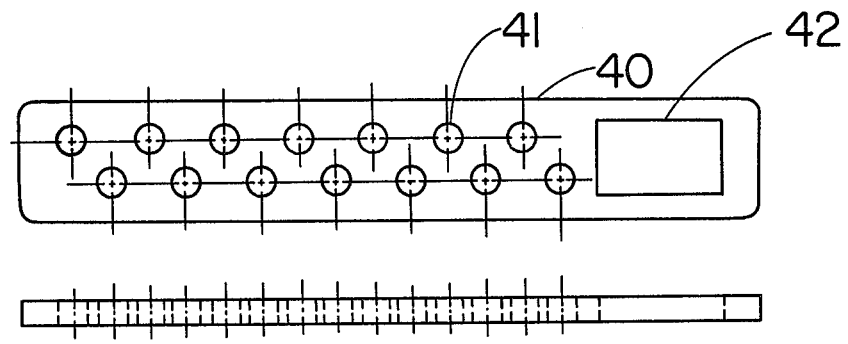
FIG. 12 is yet another alternative configuration of the extension element showing two views, a top and side view.
Figure 13:
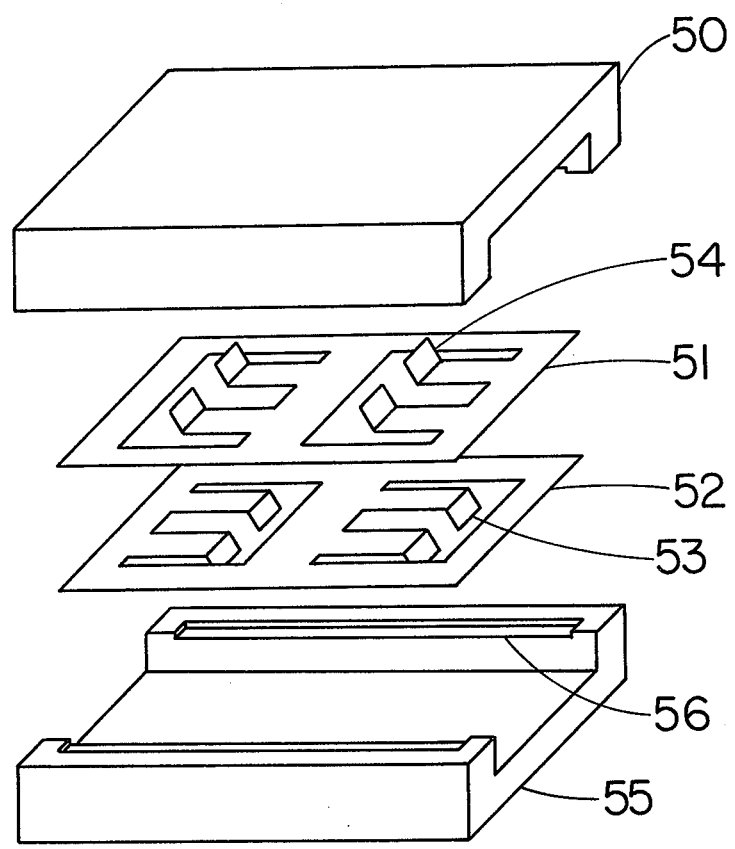
FIG. 13 is an exploded view showing the principal elements of the locking section that would be used with the embodiment of this invention illustrated with the extension unit of FIG. 12.
Figure 14:
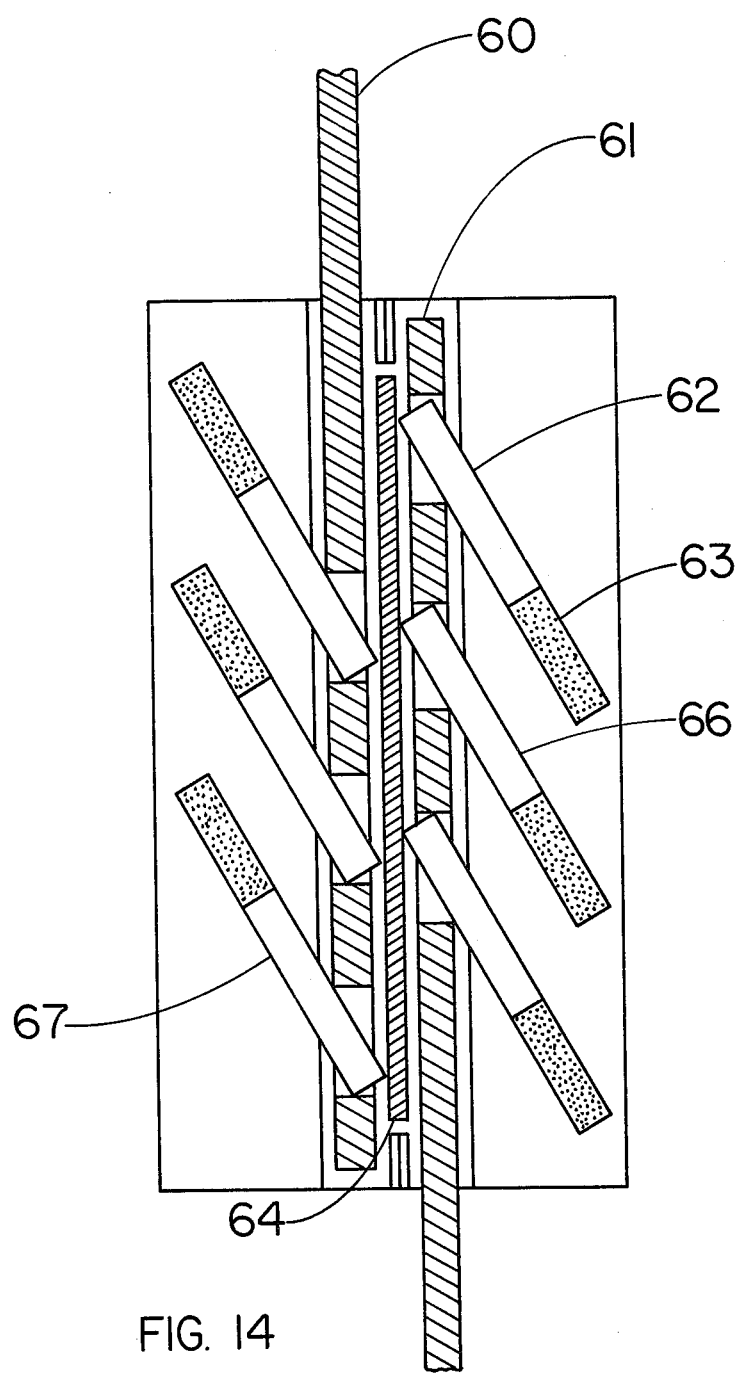
FIG. 14 is a section view of an alternate embodiment of this invention equivalent to and serving the same locking function of that described by FIG. 13.

Still another alternative to the preferred embodiment of this invention is noted in FIG. 12 which shows a plan view and a side view of this same unit of the load carrying extension element or tape. In FIG. 12, 41 represents a hole, one of a series in the extension element or tape 40, and 42 represents the same form of opening being equivalent to the opening 2 of FIG. 3. This particular extension or tape depicted in FIG. 12 would be used in pairs and would engage a fastening unit such as depicted by FIG. 13. In FIG. 13 the fingers 54 of the plate 51 would engage the holes 41 of the extension unit of FIG. 12 coming from one side. The fingers 53 of the plate 52 of FIG. 13 would engage similar holes of the extension unit coming from the opposite side of the unit. Thus by a tool, not shown, the extension units would be forced past one another and held in place by the locking of the fingers 54 against one extension unit and the fingers 53 with the extension unit coming from the opposite side. An alternative to the locking fingers 53 and 54 of FIG. 13 is shown by FIG. 14 in which locking pins 62 and 66 are engaging one extension unit 61 while three pins, one of which is 67, is engaging the extension unit 60 coming from the opposite direction. The locking pins such as 62 are held in place by a foam plastic 63 or by a mechanical spring instead of the plastic which is not depicted in FIG. 14. To prevent the fingers from one side interfering with fingers of the opposite side, a separation plate 64 of FIG. 14 is included.

In the drawings and specification there has been set forth a preferred embodiment of the invention, and although specific terms are employed, they are used in a generic and descriptive sense only and not for purposes of limitation, the scope of the invention being defined in the claims.

We claim:

1. Spinal column prostheses/orthoses which will correct problems involving scoliosis, kyphosis, spinal instability from a variety of causes, and rotational and malalignments by exerting a combination of forces on one or more pairs of vertebrae, comprising:
   A. a first elongated member having a longitudinal axis and a second elongated member overlapping said first member and having a longitudinal axis which is parallel to the longitudinal axis of said first member;
   B. adjustment means on one end of both said first and second members for controlling the longitudinal length of the combination of the first and second elongated members;
   C. a first hook means positioned at the end of said first member opposite said adjustment means, said hook means being attached to said first member through joint means by which said hook means is inserted into a hole in said first member followed by a 90° rotation of said hook means with respect to said first member, and a second hook means positioned at the end of said second member opposite said adjustment means by second joint means identical to said first joint means, each of said joint means including means for allowing rotation of each of said hook means about an axis perpendicular to the longitudinal axis of each of said members, the combination of said first and second hook means in conjunction with said first and second members and said adjustment means taken in combination to provide, upon hooking onto two chosen vertebrae, tension in the vertebrae, the amount of which is controlled by the surgeon by said adjustment means.

2. Spinal column prosthesis/orthoses as claimed in claim 1 and in addition, comprising a third elongated member having a longitudinal axis which is parallel to the longitudinal axis of said second member, said third member being attached to said second member through the use of said second hook means, and a forth elongated member, overlapping said third member and having a longitudinal axis which is parallel to the longitudinal axis of said third member, said forth member being appended to said third member by second adjustment means identical to said first adjustment means, for controlling the longitudinal length of the combination of said third and forth members; and a third hook means that is affixed to said forth member at the end opposite to the end of said second adjustment means, said third hook means having third joint means identical to said first joint means;

such the additional elongated members and hook means may be joined to said elongated members and hook means in chain fashion, the number prescribed by the surgeon, with each hook means adapted to couple about a separate and distinct vertebrae, and each combination of two elongated members with adjustment means and hook means being capable of transmitting a prescribed tension force to pairs of vertebrae equal to or different from, according to the wishes of the surgeon, the other tension forces being transmitted to other pairs of vertebrae;

and such that all hook means can be rotated 180° about axes perpendicular to the longitudinal axes of said members, resulting an a device that can produce compressive rather than tensile forces on selected pairs of vertebrae, or alternatively some hooks means can be notated 180° resulting in a device that can produce tensile forces between certain pairs of vertebrae and simultaneously produce compressive forces between other pairs of vertebrae, thereby causing a portion of the spine to experience compressive forces and another portion to experience tensile forces.

* * * * *